United States Patent [19]
Pope

[11] Patent Number: 5,136,027
[45] Date of Patent: Aug. 4, 1992

[54] METHOD FOR RENATURING PROTEINS IN THE PRESENCE OF ALKYL SULFATE DETERGENTS

[75] Inventor: Mark R. Pope, Wildwood, Ill.

[73] Assignee: Abbott Laboratories, Abbott Park, Ill.

[21] Appl. No.: 346,508

[22] Filed: May 2, 1989

[51] Int. Cl.⁵ .............................................. C07K 3/12
[52] U.S. Cl. .................................... 530/427; 530/350; 530/387.1; 530/404; 530/408; 530/391.1; 530/390.5
[58] Field of Search ............... 530/389, 387, 412, 417, 530/350, 390, 404, 408, 423, 427

[56] References Cited
U.S. PATENT DOCUMENTS

| 4,766,224 | 8/1988 | Rausch | 530/417 |
| 4,797,474 | 1/1989 | Patroni et al. | 530/417 |
| 4,801,691 | 1/1989 | Auer | 530/412 |
| 4,966,963 | 10/1990 | Patroni | 530/412 |

OTHER PUBLICATIONS

Kuusi et al, "Immunochemical Characterization of Major Outer Membrane Components from *Salmonella typhimurium*," Infection and Immunity, vol. 33, No. 3, Sep. 1981, pp. 750–757.
Ernst J. Am. Oil Chem. Soc. 57:93 (1980).
Furth, Analytical Biochemistry, 109:207–215 (1980).
Neugepauer, A Guide to the Properties and Uses of Detergents in Biology and Biochemistry (1987).

Primary Examiner—Jeffrey E. Russel
Attorney, Agent, or Firm—Thomas D. Brainard

[57] ABSTRACT

A high concentration of renaturing surfactants is added to protein systems in the presence of alkyl sulfate detergents to displace the detergent with respect to the interaction with the protein, thereby renaturing the protein and restoring its reactivity. The presence of higher quantities of detergent in the system results in smaller protein aggregates, and thus a higher reactivity and specificity as measured for the system in its entirety.

22 Claims, 1 Drawing Sheet

Covalent Immobilization of Solubilized Protein

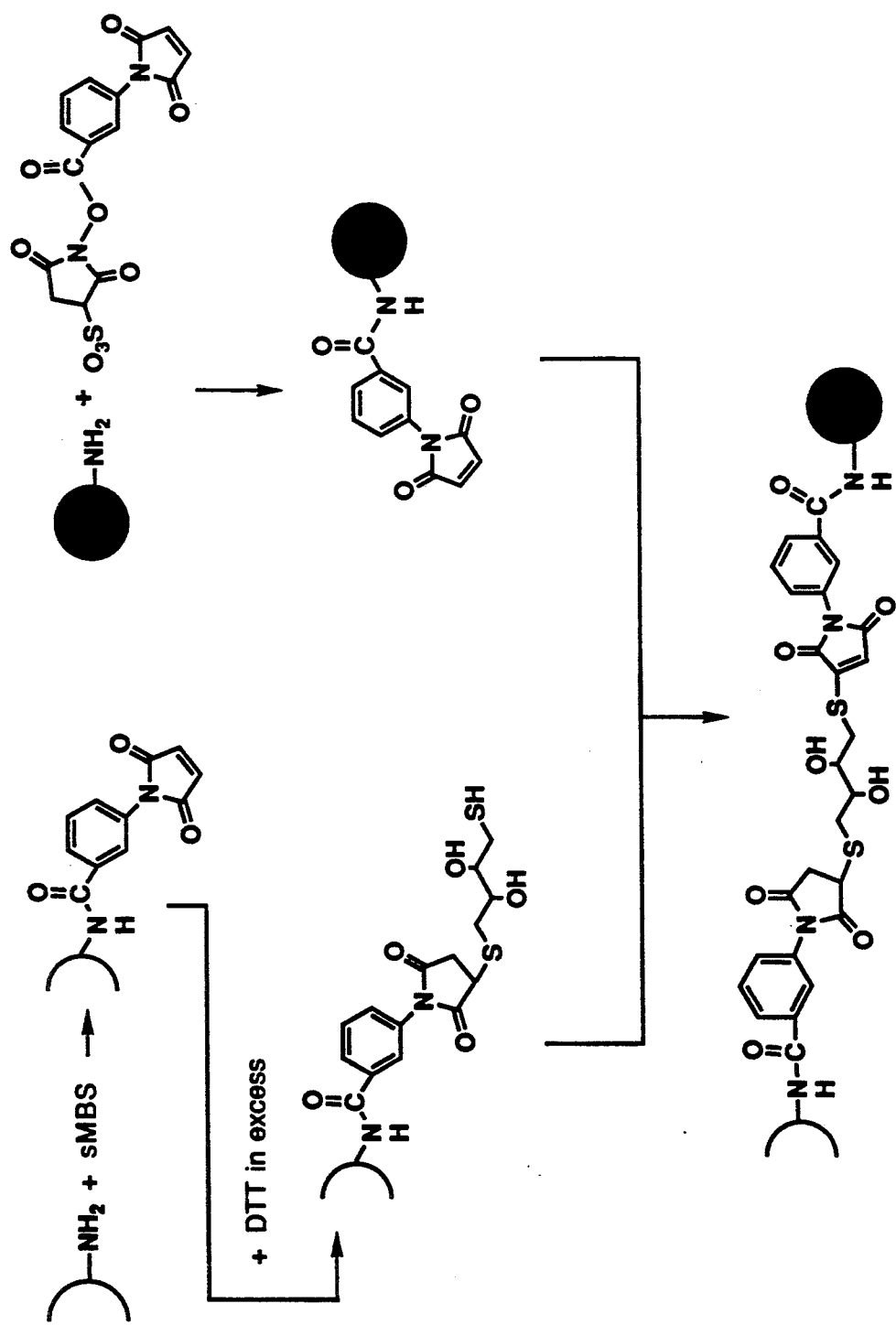
Fig. 1: Covalent Immobilization of Solubilized Protein

METHOD FOR RENATURING PROTEINS IN THE PRESENCE OF ALKYL SULFATE DETERGENTS

BACKGROUND OF THE INVENTION

The present invention relates generally to the immobilization of proteins in the presence of alkyl sulfate detergents using high concentrations of renaturing surfactants, and immuno-assays using such immobilized proteins. A related application, Ser. No. 07/346,108, is filed concurrently herewith.

In recent years, enzyme immuno-assay procedures have come into wide spread use in the diagnosis of various disorders and conditions of the human body. Such techniques, commonly referred to as EIA, make use of the mechanisms of immune systems in higher organisms. Antibodies are produced in response to the presence in the organisms of antigens which are pathogenic or foreign to the organisms. For example, the human body may produce antibodies in response to and which are capable of reacting with a particular antigen, and it is that interaction which forms the basis for many EIA techniques.

As is now well understood, antigens are typically high molecular weight proteins which have any of a variety of functional chemical groups. Antibodies are proteins produced by the immune system of the human body which have the capability of reacting specifically with those antigens. One such EIA technique which can be used to determine the presence of antibodies in body fluids is the EIA technique described in European Patent Publication No. 0 217 403 A2 published on Apr. 8, 1987. In the immuno-assays described therein, microparticles which contain reactive functional groups react with an antigen to immobilize the antigen on the surfaces of the microparticles. The immobilized antigen is then contacted with, for example, a body fluid which is suspected of containing antibodies to the antigen. The antibodies, having a specific reactivity with the immobilized antigen, become chemically bonded to the antigen which has been immobilized. The matrix is then contacted with a second reactant which contains a label having the capability of reacting chemically with the antibodies bound to the immobilized antigen, to produce a detectable response indicative of the presence and/or amount of the antibodies contained in the sample of body fluid.

Thus, the EIA technique as described in that European Patent Publication depends on the immobilization of the antigen without impairing its reactivity to specific antibodies for which a response is desired. Of course, it is also possible to immobilize antibodies specific for a desired antigenic analyte.

Many proteins or antigens which are used in such EIA techniques become insoluble as a result of the formation of aggregates among them. For that reason, such protein reagents must be used in systems in which the proteins are solubilized so that they can be immobilized on the microparticles. It has become conventional to solubilize such proteins using a surfactant such as urea, guanidine hydrochloride or alkyl sulfate detergents such as sodium dodecyl sulfate (SDS), to maintain the stability of protein in the solution so that it can be immobilized on the surface of the microparticles.

It is known that the use of SDS, while effective in promoting the solubility of antigenic proteins, can also produce problems. Detergents like SDS are often referred to as denaturing surfactants, causing the protein to unfold and thereby lose its reactivity. In systems where it is desired to covalently immobilize the protein on a solid phase test medium as is described in the aforementioned European patent publication, the denaturing effect of SDS or other alkyl sulfate detergents may result in an inactive or non-reactive protein being bound to the solid phase.

It has been proposed to replace SDS by using high concentrations of urea or guanidine hydrochloride. However, that approach has been found to produce an increase in the non-specific reactivity of the protein in various immuno-assays.

Immuno-assays are now widely used for the detection of proteins, and particularly for detecting the presence of antibodies and antigens in a given system. One of the immuno-assays which is finding ever-increasing widespread use is the assay for detecting antibodies to HIV. Several antigens have been developed, some through genetic engineering techniques, for use in detecting antibodies to HIV. Some of those are described in copending and co-owned application Ser. No. 020,282, filed Feb. 27, 1987, no abandoned, and entitled "Immuno-Assays for Antigens to HIV." Antigens used in detecting antibodies to HIV have been found to be either insoluble or poorly soluble in aqueous solution, and those solubility characteristics have prevented or impaired the immobilization of those antigens on microparticles of the kind described in the foregoing European patent publication.

The HIV antigens discussed are, like many other antigens known in the art, generally solubilized with alkyl sulfate detergents, and particularly SDS. It has been found, however, that when antigens solubilized with SDS are immobilized, the antigen proteins are at the same time denatured, rendering the immuno-assays using them ineffective. It has been found that such antigens not only lose reactivity, they at the same time lose their specificity for reaction with the antibodies found in body fluids. Thus, it has become necessary to develop a system which is capable of not only solubilizing such antigens, and other proteins requiring the presence of alkyl sulfates for solubility, but also ensuring that the specific reactivity of those antigens is retained.

Various other techniques have been used to renature, or to prevent denaturation of, proteins generally. For example, betaines have been used to prevent denaturation of enzymes solubilized with alkyl sulfates. Further, it was found that denatured enzymes could be renatured after addition of betaines and subsequent passage of the solution through an ion exchange resin to remove the alkyl sulfates. Another previously used technique employed electrophoresis to remove alkyl sulfates, resulting in the renaturation of proteins solubilized with the alkyl sulfates. Such methods, however, are not conventionally used and are impractically employed in a commercial setting as a result of the specialized and prohibitively expensive equipment employed in such techniques and the large amount of time required by those methods.

SUMMARY OF THE INVENTION

It is thus an object of the present invention to provide a method in which insoluble or poorly soluble aggregate proteins which have been solubilized by an alkyl sulfate detergent may be renatured while maintaining solubility and without adversely affecting reactivity of such proteins.

It is another object of the present invention to provide a method in which the reactivity of protein solubilized with an alkyl sulfate detergent is increased by employing a renaturing surfactant in combination with the alkyl sulfate.

It is yet another object of the invention to provide a substrate upon which proteins, such as antigens or antibodies, can be immobilized for use in an immuno-assay without adversely affecting the reactivity of the protein.

Still another object of the present invention is to provide a solid phase to which a binding protein is bound without adversely affecting the specific reactivity of the protein.

The methods and devices of the present invention reside in the uses and applications of a high concentration of renaturing surfactants in a protein system which has been solubilized with an alkyl sulfate detergent. It has been found that the use of such renaturing surfactants not only renatures the solubilized protein, but also improves the reactivity of the protein and thus ensures that the protein can be immobilized in an immuno-assay test system or "solid phase." It has been found that the renaturing surfactants employed in the practice of the present invention displace the detergent in its interaction with the protein, thereby renaturing the protein and restoring its reactivity. At the same time, the use of such denaturing, solubilizing surfactants inhibits the formation of larger aggregates, ensuring high reactivity and specificity, particularly in an immuno-assay.

According to another aspect of the present invention, antigens which have the capability of reacting with antibodies to HIV can be renatured and their reactivity restored when those antigens, solubilized with an alkyl sulfate detergent, are mixed with the renaturing surfactants used in the practice of the present invention. It has been found that such antigens can be immobilized to a solid phase in an immuno-assay and used successfully to detect antibodies to HIV with greater reactivity and specificity. This aspect also applies to other antigens and antibodies.

BRIEF DESCRIPTION OF THE DRAWING

FIG. 1 is a diagram illustrating the steps of one method of immobilizing a protein on a solid phase according to an aspect of the present invention.

DETAILED DESCRIPTION OF THE INVENTION

The present invention is not limited to the recombinant proteins developed as antigens in the detection of antibodies to HIV, and may be usefully and successfully employed in the solubilization and renaturation of other proteins which are renaturable without loss of activity. Such other proteins include other antigens, haptens and antibodies. However, since the present invention finds a particularly useful application in the immobilization of HIV antigens, the present invention will be described in reference to the recombinant proteins described in co-pending and co-owned application, Ser. No. 020,282, now abandoned.

The proteins described in the foregoing co-pending application are solubilized with an alkyl sulfate detergent, typically sodium dodecyl sulfate or SDS. It will be understood, however, that the present invention can be applied with equal facility to proteins which have been solubilized with other alkyl sulfate detergents in which the alkyl group contains 8 to 20 carbon atoms.

The concentration of the alkyl sulfate detergent typically employed in the solubilization of such proteins is determined empirically based on the particular protein employed. Typically, such proteins are solubilized with an alkyl sulfate detergent present in an amount of minimum range of about 0.05 percent to about 10 percent by volume. However, additional quantities of alkyl sulfate detergents may optionally be added to promote solubility, with solubilization optionally being further promoted by heating the aqueous system of detergent and protein.

According to the practice of the present invention, a high concentration of a renaturing surfactant is added to the alkyl sulfate detergent-solubilized protein. Suitable renaturing surfactants include the well-known class of betaine surfactants (such as N-dodecylsulfobetaine and N-octylsulfobetaine), alkyl glucosides (such as decyl glucoside and heptyl glucoside) and polyoxyethylenes (such as TWEEN-20 (from Atlas Chemical) and TRITON X-100 (from Rohm & Haas)). As is well-known to those skilled in the art, TWEEN-20 is a fatty acid ester. However, other renaturing surfactants may also be used in the practice of the present invention.

It is believed that the alkyl sulfate detergent has the effect of denaturing such proteins in solution through the unfolding of the protein chain in the presence of the detergent. The denaturation results in a loss of reactivity. The renaturing surfactant employed in the practice of the present invention displaces the detergent and is believed to form a complex with the protein to thereby renature the protein and restore its reactivity as well as specificity of reaction. Thus, while alkyl sulfate detergents result in the loss of antigenicity, the renaturing surfactants of the present invention restore the antigenicity by displacing the denaturing alkyl sulfate detergent.

The quantity of renaturing surfactant necessary to restore the reactivity of the protein in the practice of the present invention is typically determined empirically depending at least in part on the specific protein employed. It has been determined, however, that at least for TWEEN-20 and TRITON X-100, concentrations at or above the critical micelle concentration of the renaturing surfactant are necessary to effect renaturation. With some recombinant proteins of the kind described in the foregoing co-pending application, it has been found that if the amount of renaturing surfactant employed is less than 1 percent, the protein has a reactivity which is quite low. At concentrations of 5 percent by volume of the renaturing surfactant, the reactivity of the proteins is sufficient for many applications. It has also been shown, however, that the reactivity of the protein can be reduced if the amount of the renaturing surfactant is extremely high, of the order of about 20 percent by volume. It is believed that the reduction in reactivity from extremely high concentrations of the renaturing surfactant is a consequence of high viscosity and correspondingly slow reaction kinetics. Typically, the concentration of the renaturing surfactant falls within the range of 2 to 18 by volume (about 2.2 to 19.7 percent weight/volume) percent, and preferably 5 to 15 percent (about 5.4 to 16.4 percent w/v). Optimal concentrations of about 10 percent (about 10.8 percent w/v) renaturing surfactant have been found to provide maximum protein reactivity in the case of protein solubilized with SDS.

The present method is preferably used in systems requiring agents such as alkyl sulfate detergents to maintain protein solubility for immobilizing antigens or antibodies, conjugation of proteins, or chemical modification of proteins. The following examples illustrate the quantities of reagents employed to restore the activity of specific proteins in the presence of an alkyl sulfate detergent:

EXAMPLE 1

Activation of B. meg. recombinant gp-41

A sample of 0.3 mg of the recombinant HIV antigen gp-41 was solubilized in 0.1% SDS/PBS (phosphate buffered saline). No reactivity was detected for that protein. 1.0 ml of that solution was added to a reaction vessel, and 0.2 ml of 10 percent SDS was further added. 1.0 ml of 30 percent TWEEN-20 (Atlas Chemical) was added, and the combination mixed. To the mixed combination 0.3 ml PBS was added. 0.5 ml of a solution of 40 micrograms m-maleimidobenzoyl-N-hydroxysulfosuccinimide ester (sulfo-MBS, available from Pierce) per ml PBS was added. The resulting solution was vortexed and allowed to set at room temperature for one hour.

The gp-41 was linked, through the addition of the sulfo-MBS, to a hetero-bifunctional group, preparing it for immobilization on a solid medium. The protein was found to be sufficiently reactive for use in an immunoassay.

EXAMPLE 2

Activation of recombinant p-24

Fifty microliters of ten percent SDS were added per ml of 800 micrograms/ml recombinant p-24, such that the concentration of SDS in the resulting solution was 0.5 percent. The solution was heated at 40° C. for 20-30 min to drive any unsolubilized protein into solution. The protein concentration was determined by a modification of the Lowry assay (G. L. Peterson, "Analytical Biochemistry", Vol. 83, pp. 346-356, 1977). 0.47 ml of the p-24/SDS solution (containing 375 micrograms of protein) added to a reaction vessel. To this, 0.03 ml PBS, 0.5 ml 30 percent TWEEN-20, and 0.5 ml of a solution of 120 micrograms/ml sulfo-MBS in PSA were added. The resulting solution was thoroughly vortexed and allowed to set at room temperature for one hour.

The p-24 was linked, through the addition of the sulfo-MBS, to a hetero-bifunctional group, preparing it for immobilization on a solid medium. The protein was found to be sufficiently reactive for use in an immunoassay.

The renatured solubilized proteins may be immobilized on solid media for use in, e.g., immuno-assays. The solid medium provides a desirable test substrate, as, for example, disclosed in European Patent Publication No. 0 217 403 A2. The solubilized protein, e.g., an antigen, is covalently linked to the solid medium to render it immobile. The process of immobilization is illustrated in FIG. 1.

Referring to FIG. 1, and beginning at the upper left portion of the illustration, a microparticle is provided having an amine group. Such microparticles include those available commercially known as Amino-microparticles (Polysciences, Inc.). The amino microparticles are mixed with a hetero-bifunctional compound, e.g., sulfo-MBS (in the illustration, "sMBS"), which interact to produce a microparticle, to which is linked a heterofunctional group ("an activated microparticle"). Useful heterobifunctional compounds are typified by active maleimides, and include compounds capable of reacting with an amine or other reactive group on the microparticle and with a thio-group for covalently immobilizing the protein.

Following the linkage of the hetero-bifunctional group with the microparticle, the activated microparticle is reacted with dithiothreitol (present in excess) to produce a thiolated microparticle. This thiolated microparticle is illustrated in the left central portion of the figure.

The upper right portion illustrates the activation of the renatured solubilized protein according to the present invention with a hetero-bifunctional compound (e.g., an active maleimide) in preparation for covalent immobilization on a solid medium, as described above. The protein (e.g., an antigen) includes an amine group for linking with the hetero-bifunctional compound (e.g., sulfo-MBS or other active maleimides). The resultant activated protein is illustrated in the left center portion of the figure. In the presence of the alkyl sulfate detergent and the surfactant according to the present invention, the activated protein retains its reactivity and remains solubilized throughout this process.

The activated protein is covalently immobilized on the microparticle by reaction of the thiolated microparticle with the hetero-bifunctional group attached to the protein. This is illustrated in the lower portion of FIG. 1. The resulting immobilized protein retains its reactivity and may be used in immuno-assay. The methodology described is discussed in greater depth in the co-pending and co-owned application Ser. No. 07/346,108, entitled "Covalent Attachment of Specific Binding Members to a Solid Phase," filed herewith, and incorporated herein by reference.

In another method, not illustrated but known to the artisan, thio- groups existing within the protein structure are employed to covalently link the protein to a solid phase. According to that method, the solid phase is provide with a group, e.g., a hetero-bifunctional group, capable of reacting with the thio- group in the protein and thereby link to it.

A solid-phase assay device may be made, including proteins which have been immobilized according to the present invention. Such a device is disclosed in European Patent Publication No. 0 217 403 A2. The device disclosed therein comprises a substantially planar layer of material having a porous matrix of fibers, upon which are immobilized a plurality of substantially spherical microparticles (having an average diameter of from about 0.1 microns to about 10 microns), like those described herein. The device also comprises in the substantially planar layer a first, sample contacting surface and a second surface opposed to the first surface, being disposed in the device such that when the device is used in the performance of an assay, at least a portion of the sample contacting the first surface passes through the substantially planar layer to the second surface.

The microparticles used in the assay device have immobilized thereon a protein. Protein immobilization using an alkyl sulfate detergent and a high concentration of surfactant according to the present invention results in a device for conducting immuno-assays using proteins which may have been otherwise unsuitable or inefficacious as a result of solubility or reactivity characteristics. The method of renaturing and immobilizing proteins according the present invention results in greater protein reactivity and specificity as a direct result of the increased protein solubility and smaller aggregate size.

Although the present invention has been described in terms of specific embodiments and examples, the skilled artisan will understand that the invention is not limited solely to those embodiments disclosed or their equivalents.

What is claimed is:

1. A method for renaturing a protein in the presence of an alkyl sulfate detergent, comprising the steps of:
    providing a protein solubilized in denatured form with the alkyl sulfate detergent, said protein having in its native form a reactive site for binding specifically with a predetermined binding partner; and,
    without removal of the alkyl sulfate detergent, adding a concentration of surfactant effective to renature the protein, wherein the protein's reactive site regains its native reactive configuration.

2. The method of claim 1, wherein the protein is an antigen.

3. The method of claim 1, wherein the protein is an antibody.

4. The method of claim 1, wherein the alkyl sulfate detergent is sodium dodecyl sulfate.

5. The method of claim 1, wherein the surfactant is selected from the group consisting of betaines, alkyl glucosides, and polyoxyethylenes.

6. The method of claim 5, wherein the surfactant is a polyoxyethylene.

7. The method of claim 1, wherein the concentration of surfactant is at least about the critical micelle concentration of the surfactant.

8. The method of claim 1, wherein the concentration of surfactant is between about 5.4 and about 16.4 percent weight/volume.

9. The method of claim 8, wherein the concentration of surfactant is about 10.8 percent weight/volume.

10. The method of claim 8, wherein the surfactant is a polyoxyethylene.

11. The method of claim 1, comprising the further step of covalently modifying said renatured protein to introduce a linker molecule useful for immobilizing said protein to a solid phase.

12. A method for renaturing an antigen in the presence of sodium dodecyl sulfate, comprising the steps of:
    providing an antigen solubilized in denatured form with sodium dodecyl sulfate, said antigen having in its native form a reactive site for binding specifically with a predetermined antibody; and,
    without removal of the alkyl sulfate detergent, renaturing the antigen by the addition of a concentration of a polyoxyethylene effective to renature the reactive site of the antigen.

13. The method of claim 12, wherein the concentration of polyoxyethylene is about 10.8 percent weight/volume.

14. A method for solubilizing a protein comprising:
    treating an insoluble protein selected from the group consisting of antigens and antibodies with a denaturing alkyl sulfate detergent to provide a soluble protein in denatured form, said protein having in its native form a reactive site for binding specifically with a corresponding antibody or antigen; and
    without removal of the alkyl sulfate detergent, adding a concentration of surfactant effective to renature the protein, wherein the protein's reactive site regains its reactive configuration.

15. The method of claim 14, wherein the protein is an antigen.

16. The method of claim 14, wherein the alkyl sulfate detergent is sodium dodecyl sulfate.

17. The method of claim 14, wherein the surfactant is selected from the group consisting of betaines, alkyl glucosides, and polyoxyethylenes.

18. The method of claim 14, wherein the concentration of surfactant is at least about the critical micelle concentration of the surfactant.

19. The method of claim 14, wherein the concentration of surfactant is between about 5.4 and about 16.4 percent by weight.

20. The method of claim 19, wherein the concentration of surfactant is about 10.8 percent by weight.

21. The method of claim 19, wherein the surfactant is a polyoxyethylene.

22. The method of claim 14, comprising the further step of covalently modifying said renatured protein to introduce a linker molecule useful for immobilizing said protein to a solid phase.

* * * * *

UNITED STATES PATENT AND TRADEMARK OFFICE
CERTIFICATE OF CORRECTION

PATENT NO. : 5,136,027
DATED : August 4, 1992
INVENTOR(S) : Mark R. Pope

It is certified that error appears in the above-indentified patent and that said Letters Patent is hereby corrected as shown below:

Column 7, line 17, claim 1, add --renaturing-- before "surfactant".

Column 8, line 22, claim 14, add --renaturing-- before "surfactant".

Signed and Sealed this

Twenty-eighth Day of June, 1994

Attest:

BRUCE LEHMAN

*Attesting Officer*    *Commissioner of Patents and Trademarks*